United States Patent [19]

David et al.

[11] Patent Number: 4,800,874
[45] Date of Patent: Jan. 31, 1989

[54] ANATOMICAL BONE PLATE AND/OR TRANSFIXION PLATE

[75] Inventors: Thomas David; Dieter Uyka, both of Vienna, Austria

[73] Assignee: Vereinigte Edelstahlwerke A.G., Vienna, Austria

[21] Appl. No.: 73,575

[22] Filed: Jul. 14, 1987

[30] Foreign Application Priority Data

Jul. 15, 1986 [AT] Austria ................................. 1927/86
Dec. 2, 1986 [AT] Austria ................................. 3215/86

[51] Int. Cl.$^4$ .............................................. A61F 5/04
[52] U.S. Cl. .............................. 128/92 YP; 128/92 Y
[58] Field of Search ........... 128/92 Y, 92 YP, 92 YL, 128/92 YJ, 92 YF, 92 VY, 92 VW; 623/22

[56] References Cited

U.S. PATENT DOCUMENTS

| | | | |
|---|---|---|---|
| 3,577,853 | 5/1971 | Roberts ............................ | 128/92 Y |
| 3,824,631 | 7/1974 | Burnstein et al. ................ | 128/92 YJ |
| 4,120,298 | 10/1978 | Fixel ................................ | 128/92 YP |
| 4,403,606 | 9/1983 | Woo et al. ....................... | 128/92 Y |
| 4,511,335 | 4/1985 | Tatum, Jr. ....................... | 128/92 YP |
| 4,573,458 | 3/1986 | Lower .............................. | 128/92 Y |

FOREIGN PATENT DOCUMENTS

| | | | |
|---|---|---|---|
| 0100114 | 2/1984 | European Pat. Off. ........ | 128/92 YP |
| 2410057 | 7/1975 | Fed. Rep. of Germany . | |
| 8201645 | 5/1982 | PCT Int'l Appl. ............ | 128/92 YL |
| 1122305 | 11/1984 | U.S.S.R. .......................... | 128/92 YP |

OTHER PUBLICATIONS

Zimmer-U.S.A., Inc., "Z Product Encyclopedia" 1978, pp. B168 & B169, Lib. of Cong. #78-64509.

Primary Examiner—Stephen C. Pellegrino
Assistant Examiner—Ralph Lewis
Attorney, Agent, or Firm—Holman & Stern

[57] ABSTRACT

A bone transfixion plate for transfixing an acetabulum fragment to the os ilium, by screw means, following pelvic osteotomies with rotation of the roof of the acetabulum, particularly in a human patient. The plate comprises: a proximal region for application to the os ilium which is at least generally adapted for close application to the region to which it is applied; a distal region for application to the acetabulum fragment which is at least generally adapted for close application to the region to which it is applied, these regions being disposed at a mutual angle in the ventrodorsal/mediolateral plane in the range 10°-50°, preferably about 30° (or, in a plate for a dog, the angle in the equivalent plane is 20°-70° and preferably 30°-60°); and for forming this angle a generally wedge-shaped transition zone between the two regions, the greater width of the transition zone being preferably at the ventral edge of the plate (or, in a plate for a dog, preferably at the dorsal edge). The plate is an element of a transfixion system which may include wire loops passed over two screws in the region of the foramen ischiadicum, and additional transfixion means to the os ischium and os pubis comprising one wire loop passed over two screws, one of which is affixed to the acetabulum fragment and the other of which is affixed to the os pubis.

19 Claims, 6 Drawing Sheets

ANATOMICAL BONE PLATE AND/OR TRANSFIXION PLATE

BACKGROUND OF THE INVENTION

1. Field of the Invention

The invention relates to a bone transfixion plate for transfixing an acetabulum fragment of the os ilium to the os ilium following a hip osteotomy with rotation of the roof of the acetabulum, in a human patient, wherein a section is performed on the acetabulum in the region of the os ilium and os ischium, which section may employ a single common cut, particularly a cut which is essentially along a cylindrical surface, and a second section is performed in the region of the os pubis, employing a cut which may particularly be planar, and wherewith the plate is affixed stably to the facies glutea of the cranial pelvic column of the ala ossis ilii.

2. Description of the Prior Art

There are various techniques of double and triple osteotomy for hip socket rotation in treating hip joint dysplasia, particularly in human medicine. The one considered most successful is a triple osteotomy wherein the section of the acetabulum is approximately spherical, the advantage being that the acetabulum can then be shifted laterally as well as ventrally. For this triple technique, sections must be performed on the os ilium, os ischium, and os pubis.

First the ischial osteotomy is performed, with a section from the foramen ischiadicum to the foramen obturatum; the os ischium then remains held dorsally by ligaments which connect to the tuber ischii and spina ischiadica, and other ligaments which pull toward the sacrum. It should be noted in this connection that the foramen obturatum is involved, and because of the condition that the os ischium must be sharply resected to the membrana obturata, strips of bone which are formed must be sectioned in order to be able to eventually rotate the acetabulum.

Then the osteotomy of the os pubis is performed, close to the hip joint. The line of the osteotomy is parallel to the acetabulum, at a slight inclination into the foramen obturatum, in order to ensure some bone contact following the acetabulum rotation, thereby facilitating rapid bone healing.

The third stage is the osteotomy of the os ilium. A Steinmann pin is inserted in advance into the pelvic bone to assist later on in rotating and swinging the acetabulum parallel to the planned osteotomy which is inclined medially. The iliac osteotomy is planar, performed first with an oscillating saw and then with chisels.

Following the osteotomies, the acetabulum is then rotated and swung, over the head of the femur, with the extent of such rotation and swinging being at least based on the need prior to the surgery to brace the head of the femur in order for it to come under the roof of the acetabulum. For this purpose, the roof of the acetabulum is pulled over the head of the femur on a Steinmann pin, and where required is also pulled forward, and the medial ramus of the os pubis is also pressed so as to rotate upward. Then the acetabulum is urged medially by manual force, and a good contact of the acetabulum fragment with the os pubis is created.

There should be substantial superposition by the sclerosing zone of the roof of the acetabulum and by the facies lunata, to become disposed over the head of the femur, because this creates the proper surface for receiving and transmitting compressive forces generated by stresses from the leg. The subsequent transfixion of the acetabulum is by Kirschner wires inserted into the acetabulum fragment in four different directions, with the far ends of said wires being pinched off and bent around on the crest of the ilium. This type of transfixion is difficult, often unstable, and often leads to an unsatisfactory outcome, wherein the acetabulum is not firm, the healing of bone is sharply retarded, and the patient must spend many weeks bedridden in a trunk-pelvis cast.

A basic reason for these problems is the unstable fixation achieved by Kirschner wires which are, however, necessary. A major reason why Kirschner wires are needed is that the iliac osteotomy is planar, wherewith when the acetabulum is swung ventrally and laterally an open wedge-shaped gap is created between the ala ossis ilii and the acetabulum fragment, and as a rule this gap must be filled by a wedge of bone which is sawed out of the crest of the ilium and is implanted in said gap; and accordingly the resulting three-body system must be transfixed and also must be amenable to new bone growth.

In a completely different technical context from this invention, a bone plate applicable in the acetabulum region is disclosed in Ger. AS No. 24 10 057, for forming an artificial border for the roof of the acetabulum without otherwise modifying the hip joint, in particular without performing an osteotomy on the hip bone (os coxae). This known plate is fixed to the os ilium by two proximal lug strips with a recess between them for accommodating the base of the crest of the ilium. The plate rests on the roof of the acetabulum, and the distal region of the plate, which is bent-in ventrally, forms the border of the roof of the acetabulum. In other words, the proximal region of the acetabulum (the "roof" of the acetabulum) is widened, primarily in the lateral direction, in order to prevent luxation of the head of the femur in the proximal direction. The purpose of this known plate, and accordingly its geometric configuration, are completely different from those of the plate of the instant invention.

BRIEF SUMMARY OF THE INVENTION

The present invention resulted from the discovery that after triple osteotomies the acetabulum can be stably transfixed to the facies glutea of the cranial pelvic column of the ala ossis ilii by means of a specially-shaped plate, an it is no longer necessary to resort to Kirschner wires and the wedge-shaped bone graft from the crest which is interposed in the wedge-shaped gap.

The anatomical bone plate of the invention is characterized in that the plate comprises a proximal region for application to the ala ossis ilii, in particular which proximal region is at least generally fitted to the region to which it is applied. The plate further comprises a distal region for application to the acetabulum fragment, in particular which distal region is at least generally fitted to the region to which it is applied, whereby these regions are disposed at a mutual angle which is in the range 10–50°, preferably about 30°, and whereby a generally wedge-shaped transition zone is provided between the proximal and distal regions, with the maximum width of the wedge being preferably at the ventral edge of the plate.

This anatomical transfixion plate is fastened by screws to the ala ossis ilii and the acetabulum fragment, and in one embodiment the transition zone of the inventive plate supports the osteotomy surface of the acetabulum fragment, which surface projects beyond the outer surface of the ala ossis ilii due to the surgical shifting of the acetabulum fragment, in particular the ventral rotation and lateral inclination of the acetabulum fragment, with the support being in the distal direction, i.e. against the stress applied from the leg.

When the anatomical bone plate of the invention is used, it is possible to achieve, in particular, stable transfixion of the roof of the acetabulum and the ala ossis ilii by means of compression osteosynthesis, whereby load can be applied to the hip joint and leg at an early date. Thus the function of the plate involves primary load-stable transfixion. The result is rapid postoperative mobilization of the patient.

Advantageously, the plate is stably fixed to the ala ossis ilii such that said plate is applied against the optimum pressure-accommodation region of the ala with regard to the 0-position of the femur, namely the ventral region of the ala, slightly distally of the tuberculum gluteum, beginning approximately one finger's width dorsally of the spina iliaca anterior superior and the spina iliaca anterior inferior and extending approximately up to the linea glutea anterior, particularly in the ventral part thereof between the supporting parts of the cranial and caudal columnae of the pelvis.

An even more significant advantage is obtained if the iliac osteotomy required for rotation of the roof of the acetabulum is not performed as a planar cut according to the state of the art, but so as to yield, in particular, an essentially cylindrical osteotomy surface between the acetabulum fragment, os ilium, and os ischium, for shifting the acetabulum fragment ventrally and laterally, whereby (by said essentially cylindrical surface) the close contact between the acetabulum fragment, ala ossis ilii, and ischium is created which contact is so important for biomechanical load transmission from femur to acetabulum to os ilium, and for postoperative bone healing.

This osteotomy line, which extends along the boundary of the incisura ischiadica major in order to maintain congruence conditions to assure good contact between the acetabulum fragment and the ala ossis ilii, when employed in conjunction with use of the inventive anatomically close fitted bone plate (transfixion plate), provides a direct, use-stable and load-stable compression osteosynthesis between the os ilium and the acetabulum fragment without interposing a bone wedge, whereby the hip joint and leg can bear a load practically immediately. In addition, reestablishment of bone tissue is unhindered without the standard multiweek immobilization by a trunk-pelvis cast, and rapid postoperative mobilization is therefore possible.

The osteotomy at a distance of at least 10 mm, preferably farther, from the edge of the acetabulum, also ensures close bone contact between the acetabulum fragment and the os ischium without having to narrow the pelvis medially.

The osteotomy of the os pubis is advantageously planar (as is that of the os ischium), with the plane of the cut being approximately perpendicular to the crista obturatoria. This cut location also ensures good bone contact between the acetabulum fragment and the os pubis after the shifting of the roof of the acetabulum.

Because the anatomical bone transfixion plates of the invention are shaped for close contact against the ala ossis ilii and the acetabulum fragment, obviously different plate profiles are required for the left and right sides of the pelvis, as well as fine adjustments to the bone surface. The shape and size of the plates is carefully matched in advance to the proximal and distal regions to which they will be applied following the shifting of the roof of the acetabulum, so that minimal corrections to their configuration will be required intraoperatively. The angle between the proximal and distal regions of the plate is adjusted to the dimensions and type of the shifting of the roof of the acetabulum, taking into account the indications and the surgical requirements.

The case may also arise that after the acetabulum fragment has been shifted (particularly after it has been rotated ventrally and inclined laterally) it must be translated medially, for biomechanical reasons, by a distance of, e.g., 4–10 mm. The result of this will be that the osteotomy edge, i.e., surface, of the acetabulum fragment in its final position will no longer project laterally beyond the exterior surface of the os ilium, or will project only slightly, so that there will no longer be a need to support the osteotomy edge against the transition zone of the transfixion plate in the proximal direction, but only to support the transition zone of the transfixion plate in the dorsal region against the osteotomy surface of the os ilium in the proximal direction.

Toward this end, an additional feature of the inventive transfixion plate is that the generally wedge-shaped transition zone is configured to rest against the osteotomy surface of the acetabulum fragment and/or against the osteotomy surface of the os ilium.

It may be medically indicated to employ both of these support options simultaneously; e.g., when the dorsal part of the acetabulum fragment is swung medially and the ventral part is swung laterally, whereby the dorsal part will be recessed under the osteotomy surface of the os ilium, and the said ventral part will project beyond the exterior surface of the os ilium.

Therefore, according to another feature of the transfixion plate of this invention, an essentially wedge-shaped transition zone for application against the osteotomy surface of the acetabulum fragment is adjoined dorsally by an essentially wedge-shaped transition zone for application against the osteotomy surface of the os ilium.

In particular, the inventive anatomical bone transfixion plate is configured such that the regions of the plate at the side directed toward the acetabulum fragment and extending to the transition zone have an edge which matches the osteotomy, which edge preferably has a generally circular arcuate shape, the radius of which depends on the size of the patient. Preferably, the inventive plate is curved in all three dimensions to conform to the contours of the bone surfaces in the application region.

As mentioned above, the plate of the invention is screwed (by means of screws) into the ala ossis ilii and the acetabulum fragment under compression. The screws used are corticalis screws. In thus mounting the inventive plate, eccentric countersink holes are provided on the plate proximally and distally, whereby the ala ossis ilii and the roof of the acetabulum are forced together by the tensile screw principle.

An effort is made to ensure that the regions of the inventive anatomical bone transfixion plate which contact the bones conform closely to the contours of the facies glutea to enable tight application to the surface.

The inventive bone transfixion plate may be used without problems for human patients age 10–45.

BRIEF DESCRIPTION OF THE DRAWINGS

The invention will be described in greater detail hereinafter with reference to the accompanying drawings which show various exemplary embodiments and wherein:

FIG. 14 is an X-ray projection of the acetabulum region, with a construction superimposed thereon for determining a polygonal osteotomy procedure in the hip bone;

FIG. 15 is an X-ray projection according to FIG. 14, after a completed osteotomy and rotation of the acetabulum;

FIG. 16 is a schematic elevational view of the situation according to FIG. 15.

DETAILED DESCRIPTION

The views in each case are of the left side of the pelvis, and of corresponding left-side transfixion plates.

Figure 1:
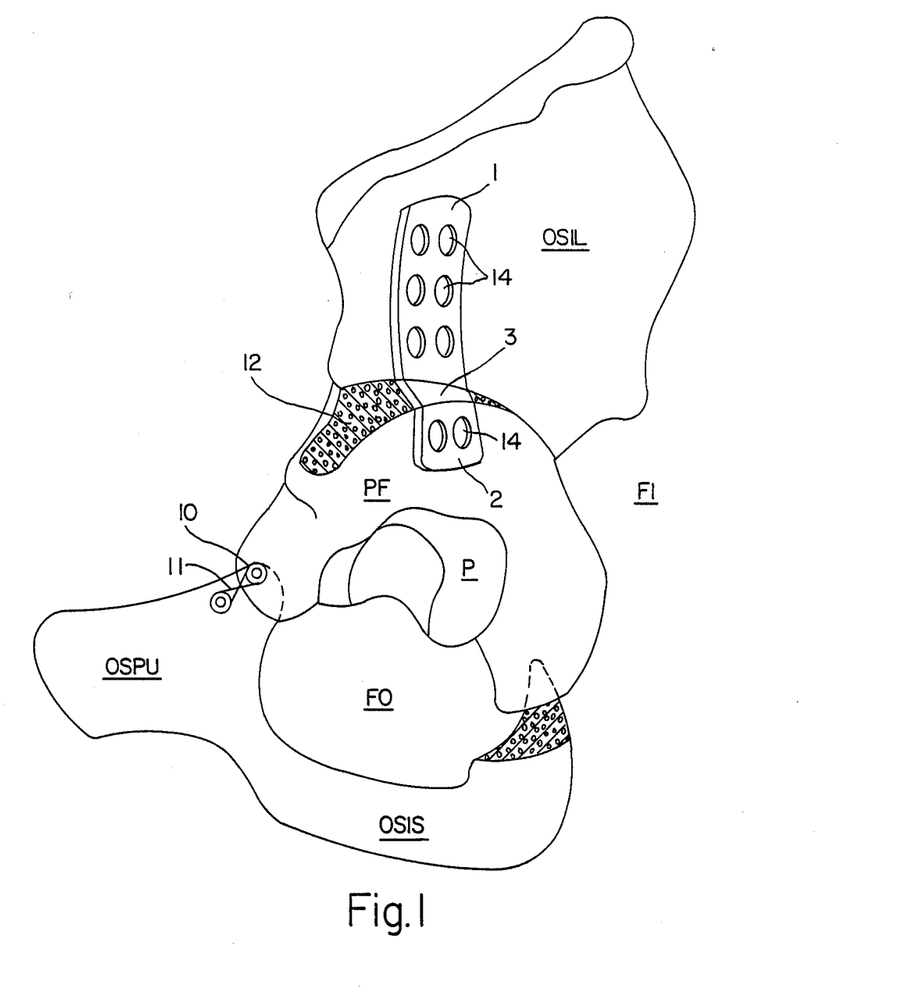
FIGS. 1 and 2 are schematic elevational views showing the transfixion of a fragment of the acetabulum in a human.

FIG. 1 is a ventrolateral view of a transfixion of the roof of the left acetabulum, following a completed threefold osteotomy with shifting, including angular shifting, of the roof of the acetabulum ventrally and laterally, i.e. rotation ventrally and generally laterally. A result of said shifting is that a part of the osteotomy surface 12 (hatched region) on the acetabulum fragment PF extends ventrolaterally beyond the external surface of the os ilium, designated OSIL. The acetabulum is designated "P", and the acetabulum fragment PF. The foramen obturatum and foramen ischiadicum are designated FO and FI, respectively, It is seen that the osteotomy of the os ilium is, in the present Example, essentially cylindrical in shape. Preferably, depending on the particular operative situation, the aim should be for the osteotomy to be spherical, so as to attain maximum congruence after the shifting of the roof of the acetabulum. It is a function of the transfixion plate 1–3, which is applied in the ventral region of the ala ossis ilii, to press the acetabulum fragment, designated PF, and the os ilium against the osteotomy surface between them, whereby the projecting osteotomy edge of the acetabulum fragment is buttressed in the distal direction.

The osteotomy surface on the os ischium, designated OSIS, is also shown as a hatched region.

The means of transfixion between the os pubis, designated OSPU, and the acetabulum fragment is shown as a wire loop 11 over two screws 10.

As seen in FIG. 1, the proximal region 1 of the transfixion plate is affixed by screws 15 (FIGS. 4a and 4c) in screw holes 14 to the ventral region of the ala ossis ilii, and the distal region 2 of the transfixion plate is affixed by screws 15 in screw holes 14 to the acetabulum fragment. The transfixion plate has a transition zone 3 between its two regions 1 and 2, which transition zone is wedge-shaped with the wide edge of the wedge being on the ventral side, and which zone supports a part of the region of the osteotomy surface 12 which extends ventrolaterally beyond the os ilium, the support being distally directed. In a sense, the wedge-shaped zone 3 acts as a lateral extension of the os ilium. The wide edge of the wedge is on the ventral edge of the plate.

Figure 2:
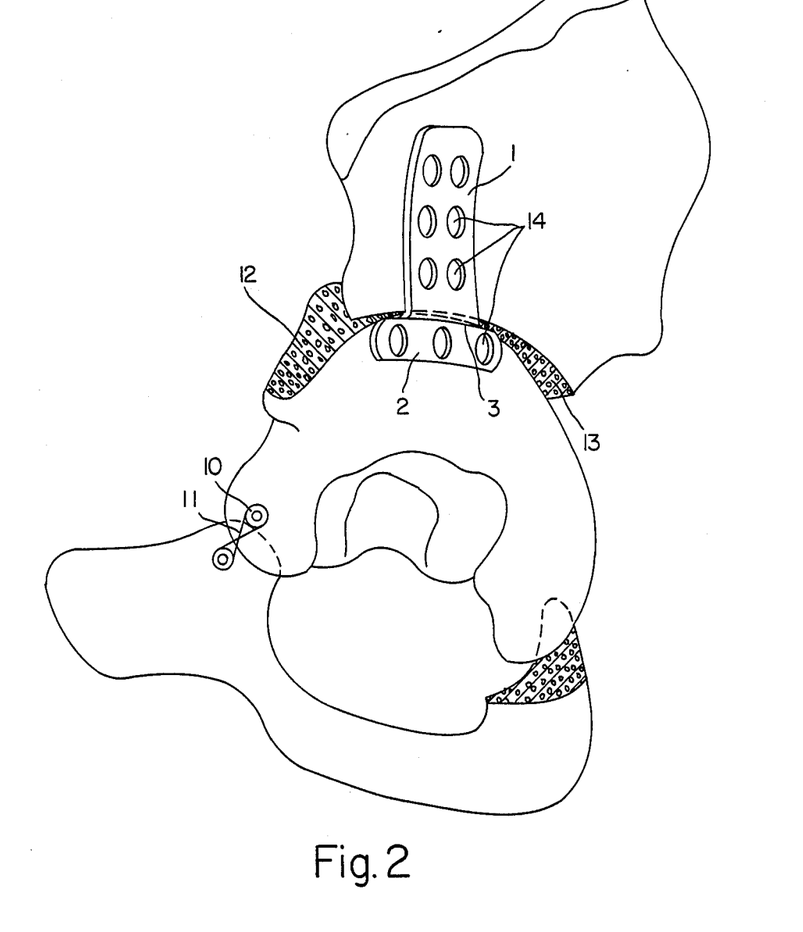

FIG. 2 is an illustration corresponding to FIG. 1, but in FIG. 2, as seen, the acetabulum fragment has been substantially medialized, i.e., shifted medially, so that the osteotomy surface 12 of the acetabulum fragment no longer extends ventrolaterally beyond the exterior surface of the os ilium, but is approximately flush with the os ilium in the ventral region of the latter, and in fact with progression dorsally the said surface 12 extends increasingly medially inward underneath the osteotomy surface 13 of the os ilium. It is seen from FIG. 2 that the transfixion plate is adapted to the geometric configuration (as is the case in FIG. 1), and provides support by conforming to the respective surfaces in the region over which it extends, whereby the wedge-shaped transition zone 3 widens with progression dorsally, extends under the osteotomy surface 13 on the os ilium, and can be said to form a lateral extension of the osteotomy surface 12 of the acetabulum fragment for the purpose of supporting surface 12 on the os ilium in the proximal direction, i.e., for the purpose of force transmission from acetabulum to ilium in the proximal direction. The os pubis is appropriately resected to enable medialization and, in some cases, lateral inclination of the acetabulum fragment.

Figure 3:
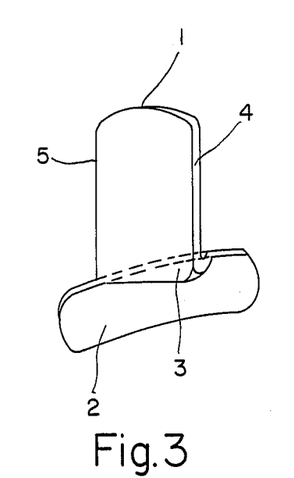
FIG. 3 is a perspective view of a plate form for use according to the invention as shown in FIG. 1.
Figure 4:
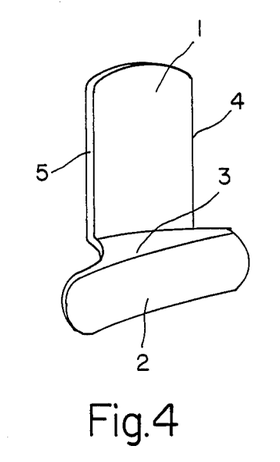
FIG. 4 is a view similar to FIG. 3 showing a plate form, i.e., intermediate workpiece before final machining, for use according to the invention as shown in FIG. 2.

FIGS. 3 and 4 are schematic medioproximal views of basic forms of transfixion plates corresponding to the configurations of FIGS. 1 and 2, respectively, which plates are juxtaposed for comparison. Here, 4 is the ventral edge and 5 is the dorsal edge.

Figure 4A:
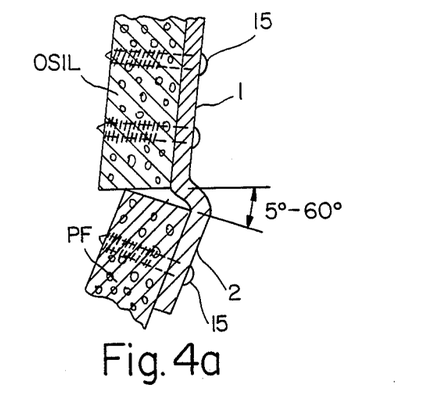
FIGS. 4a–4d are cross-sectional and perspective views showing advantageous plate forms.
Figure 4B:
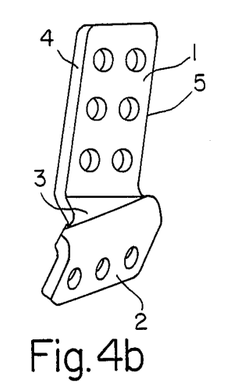

FIGS. 4a and 4b are, respectively, a cross-section and a perspective view of a transfixion plate, particularly for humans, whereby the acetabulum fragment PF is rotated, i.e. swung around the vertical axis, and inclined outwardly with respect to the os ilium OSIL. The angle of the inclination shift is 5–60°. The angle between the distal and proximal regions 1, 2 of the plate is also 5–60°.

Figure 4C:
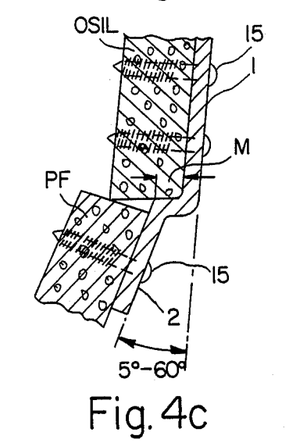
Figure 4D:
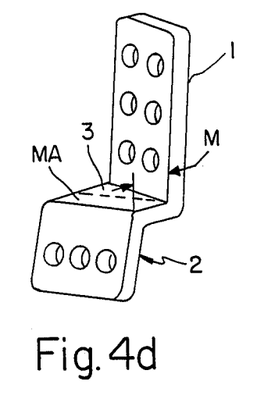

FIGS. 4c and 4d are, respectively, a cross-section and a perspective view of a transfixion plate, particularly for humans, whereby the acetabulum fragment PF is rotated, i.e. swung around the vertical axis, inclined outwardly and shifted medially. The medialization M is less than or equal to 13 mm, preferably 5–13 mm, depending on the size of the patient. The angle of inclination between the os ilium OSIL and the acetabulum fragment PF is set to 5–60°, and the angle between the distal and proximal regions 1, 2 of the plate is also 5–60°.

The length of the ventral end of the transition zone 3 thus corresponds to the required medialization M. The transition zone 3 widens with progression dorsally from the ventral end, in accordance with the horizontal angle between the proximal and distal regions 1, 2 of the plate. The transition zone 3 thus comprises a medialization region MA (determined by the desired medialization) and a wedge-shaped region (determined by the horizontal angle between the said proximal and distal regions 1, 2. The maximum horizontal width on this transfixion plate is on the dorsal edge.

Figure 5:
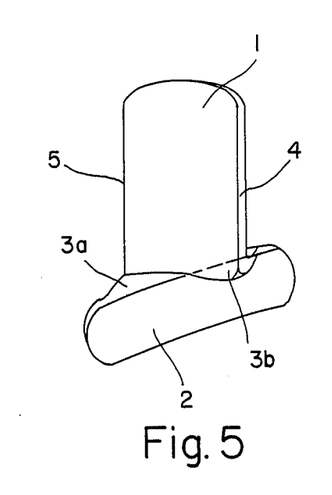
FIG. 5 is a perspective view of a plate form in which an essentially wedge-shaped transition zone for application against the osteotomy surface of the acetabulum fragment is adjoined dorsally by an essentially wedge-shaped transition zone for application against the osteotomy surface of the os ilium.

FIG. 5 is a schematic view in the manner of FIGS. 3 and 4, of an embodiment of a transfixion plate wherein both of the above-described support configurations are combined. The use of such a plate is indicated when the lateral osteotomy edges of the os ilium and that of the acetabulum fragment intersect in the region of the transfixion plate, when the acetabulum fragment is in its final position ready to be affixed. The combined plate has a laterally projecting wedge-shaped transition zone 3a on its dorsal side and a medially projecting wedge-shaped transition zone 3b on its ventral side, with the zone 3a serving to support the osteotomy surface 13 on the os ilium and the zone 3b serving to support the osteotomy surface 12 on the acetabulum fragment. The size and orientation of the wedge-shaped zones 3a, 3b on the plate depend on the desired final position of the acetabulum fragment.

Figure 6:
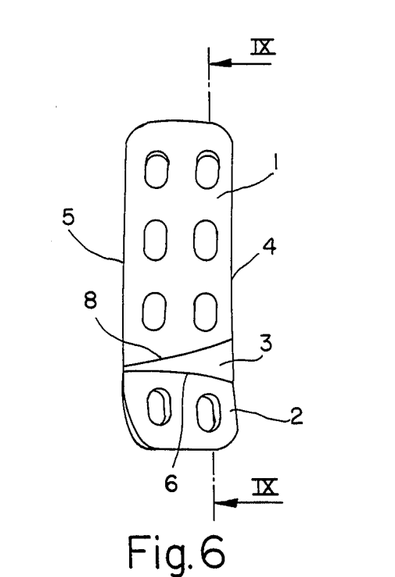
FIG. 6 is an elevational view of a plate form of the type of FIG. 3.
Figure 7:
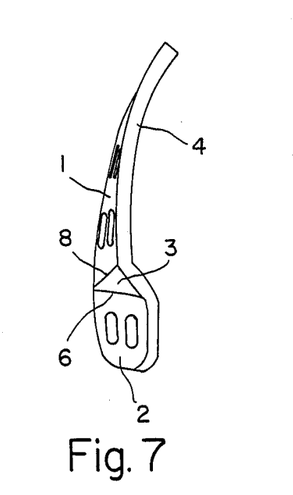
FIG. 7 is a left side view of FIG. 6.
Figure 8:
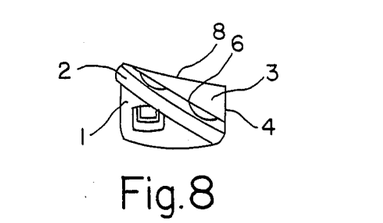
FIG. 8 is a bottom view of FIG. 6.
Figure 9:
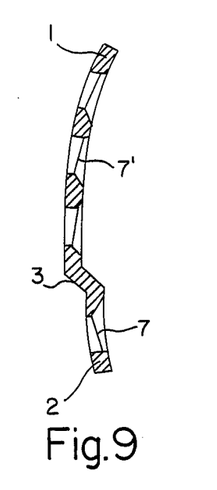
FIG. 9 is a cross-sectional view taken along line IX—IX of FIG. 6.

The plate according to FIGS. 6–9 is three-dimensionally curved. FIG. 6 is a medial view, i.e. a view toward the surface of the plate which surface comes to lie against the hip bone; FIG. 7 is a ventral view, i.e. dorsally directed; FIG. 8 is a distal view; and FIG. 9 is a cross-section through line IX—IX of FIG. 6.

The plate has a longer proximal region 1 with six screw seats 7', and a shorter distal region 2 with two screw seats 7. A wedge-shaped transition zone 3 joins these two regions, with the wide part of the wedge being at the ventral edge 4 of the plate. The regions 1 and 2 considered from the dorsal edge 5 of the plate are at an angle to one another (see especially FIG. 8), whereby dorsal edge 5 practically follows a single curved line, while ventral edge 4 has two bends through obtuse angles (see especially FIG. 7). The transition edges 6 and 8 between the transition zone 3 and, respectively, the distal zone 2 and the proximal zone 1, both have the shapes of circular arcs.

FIG. 9 shows the asymmetric countersinking 7, 7' of the screw seats, wherewith the countersinking 7 of the seats in the distal region 2 has one direction of inclination, and the countersinking 7' of the seats in the proximal region 1 has another direction of inclination. Accordingly, the screws (not shown) are not inserted acially into the seats, but in the distal region they are inclined slightly distally, and in the proximal region they are inclined slightly proximally. When the screws are installed, the wedging action of the countersunk heads of the screws on the converging surfaces of the countersinking produces a tensile stress on the plate between the proximal and distal regions 1 and 2. Due to the rigidity of the plate, the effect of this is to force together the two bone pieces being joined by the plate, namely the os ilium (screwed to the proximal region 1 of the plate) and the acetabulum fragment (screwed to the distal region 2 of the plate), whereby the abutting end surfaces of these bone pieces are pressed together.

Figure 10:
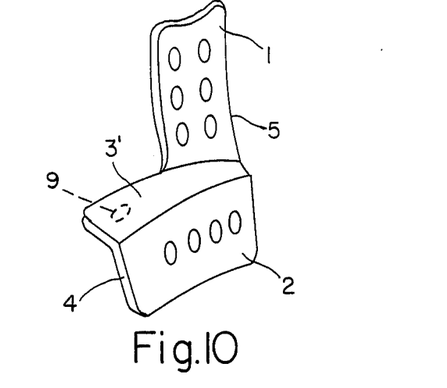
FIGS. 10–13 are perspective views of further embodiments of plate forms according to the invention.

FIG. 10 shows a plate with a transition zone 3' and distal region 2 which are wider than its proximal region 1, with the additional width being in the ventral direction. In this way, complete support is provided for the projecting edge region of the osteotomy of the acetabulum fragment. If desired, a short screw (not shown) can be inserted in the distal direction into the acetabulum fragment in the wide part of the transition zone 3'. The screw seat for this is shown by dashed line 9.

Figure 11:
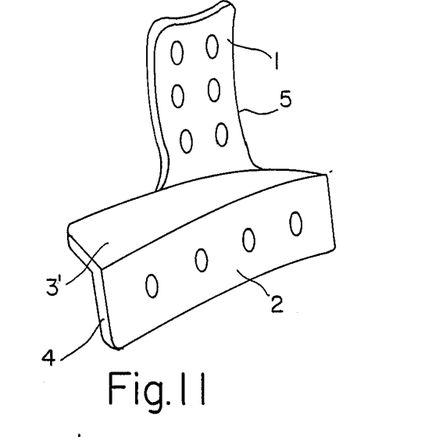

FIG. 11 shows a plate similar to that of FIG. 10, wherein the transition zone 3' and the distal region also have additional width beyond the proximal region 1 in the dorsal direction.

Figure 12:
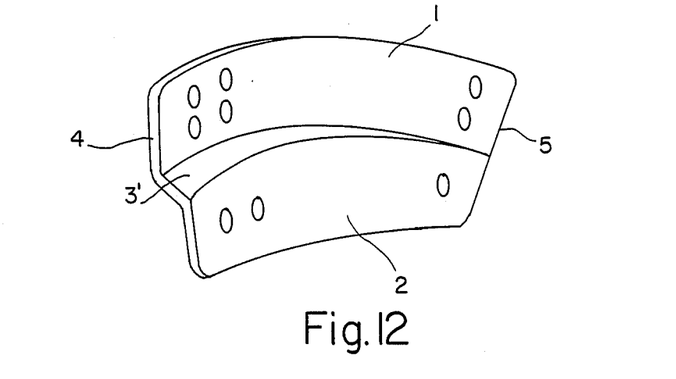

FIG. 12 shows a plate, the proximal region 1 of which extends over the osteotomy of the os ilium in a region up to the foramen ischiadicum, and the plate is screwed on with screws (not shown) at its ventral and dorsal end regions, whereby additional transfixion in the region of the foramen ischiadicum is achieved.

Figure 13:
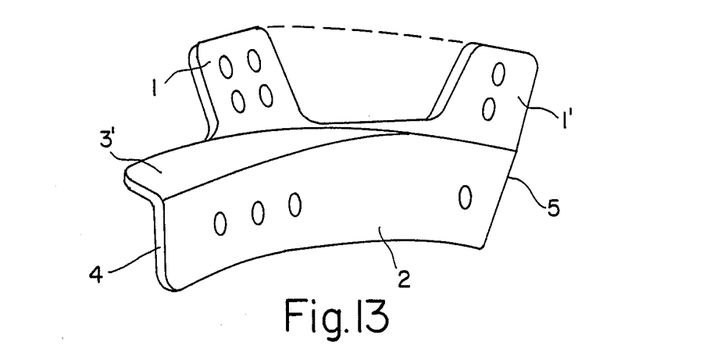

FIG. 13 shows a similar plate to that of FIG. 12, wherein the transition zone 3' and distal region 2 are wider than the proximal region 1, with the additional width being in the ventral direction, in a manner similar to FIGS. 10 and 11. The middle section of the proximal region 1 is absent, so that the proximal region essentially comprises two bent-over lugs, with the ventral lug 1 serving for fixation between the parts of the cranial and caudal columnae of the pelvis which parts bear weight, while the dorsal lug 1' serves for fixation in the region of the foramen ischiadicum. The proximal region 1 of the plate may also have the middle section filled in as per the embodiment of FIG. 12 (dashed lines in FIG. 13); and in the embodiment according to FIG. 12 the middle section may be absent.

The figures clearly indicate the three-dimensional curvature of the plate for close fitting of the plate against the ala ossis ilii and acetabulum fragment. Thus, it is seen from FIG. 9 that the proximal region 1 is convex to the ala ossis ilii when region 1 is considered in the proximal-distal direction; and it is seen from FIG. 8 that the distal region 2 is concave to the acetabulum fragment when region 2 is considered in the ventral-dorsal direction. Further, it is seen from FIGS. 7, 8, 10 and 11 that in addition the proximal region 1 is concave to the ala ossis ilii when region 1 is considered in the ventral-dorsal direction; and it is seen from FIGS. 9–13 that the distal region 2 is convex to the acetabulum fragment when region 2 is considered in the proximal-distal direction.

If desired, the embodiments of FIGS. 10–13 may be modified so that the transition zone 3' which has been extended in the ventral direction does not support the entire laterally extending osteotomy surface on the acetabulum fragment but only the lateral marginal region thereof. Accordingly, the extended region 3' will be narrower than a configuration would be which followed the wedge angle, and the maximum width of the wedge-shaped transition zone will not be disposed on the ventral edge 4 of the plate. With this embodiment, a screw cannot be inserted in the dorsal direction.

An ordinary bone transfixion plate can be substituted for a wire loop fastening 10, 11 between the acetabulum fragment and the os pubis.

The transfixion plate may be made from any suitable material, but preferably from the group of stainless steel alloys.

As mentioned above, the final osteotomy of the os ilium should be performed after the angular and other shifting of the roof of the acetabulum, in order to maintain maximal congruence. A spherical osteotomy should be considered the ideal for this purpose, from a geometric standpoint. However, this is difficult to produce surgically. It has been discovered that a linear polygonal cut, which is more practicable to achieve surgically, provides a good approximation to a spherical osteotomy. The approximate angle of the polygon is determinable based on the X-ray diagnosis. The tentative osteotomy lines, which are of equal length to the extent possible and are mutually equiangular, are laid out along a circular arc (see FIG. 14), whereby at least two linear partial osteotomy lines should be plotted for the os ilium.

A completed such osteotomy can be seen in FIG. 16, where the view is analogous to that of FIGS. 1 and 2. It is seen that, in the dorsal region, the acetabulum fragment is slightly shifted in the medial direction (similarly to FIG. 2), so that, in the region of the transfixion plate (not shown), the osteotomy surface on the ventral region of the acetabulum fragment projects laterally with respect to the lateral osteotomy edge of the os ilium, while in dorsal regions the osteotomy surface of the acetabulum fragment is recessed medially with respect to the lateral osteotomy edge of the os ilium. This corresponds to the use of a plate according to FIG. 5, which plate is adjusted, in the configurations of its edges, to the use of a linear cut in the osteotomies. The linear osteotomies on the os ilium and os ischium are seen clearly in FIG. 16. The geometry of the osteotomy of FIG. 16 is indicated in FIGS. 14-15, which are medial views.

FIG. 14 is a schematic illustration of a left hip joint in the plane of the os ilium. This kind of picture can easily be produced by X-ray. In doing so, the following conditions should be observed: The X-ray source should be centered with respect to the joint; the direction of irradiation should be perpendicular to the plane of the ala ossis ilii, and approximately aligned with the os pubis; and the X-ray source should be as far as possible from the plane of the ala ossis ilii and from the film plane, which is parallel to the ala ossis ilii.

This picture aids in establishing the osteotomy cuts in the os ilium. With the use of various three-dimensional X-ray pictures of the hip joint, the approximate shift angle (rotation angle) for the acetabulum fragment can be established prior to surgery; in particular the main angle, through which the acetabulum fragment is shifted ventrally, can be established. This angle may be in the range 25-45° (often in the range 28-38°), with an angle of approximately 38° being generally required in cases of severe hip joint dysplasia. At the same time, these X-ray pictures are used to determine the position of the center of the acetabulum.

One of the possible approximation techniques for establishing the osteotomy cuts in the os ilium is illustrated in FIG. 14. A line A along the ventrodistal side of the incisura ischiadica major is extended in the proximal direction. This line represents the first cut line. Then a tangent T1 to the curvature of the os ilium at the incisura ischiadica major and passing through the center PZ of the acetabulum is drawn, along with a tangent T2 to said curvature which line T2 is also tangent to the ventroproximal edge of the acetabulum P. It turns out that the intersection point I of the aforementioned extension line A with the tangent T1, and the intersection point II of extension line A with the tangent T2, are good approximations of the first apex of the desired polygonal line, whereby point I represents a small rotation angle and point II represents a large rotation angle. FIG. 14 shows a plotting of a rotation by a large angle. The procedure is to begin at point II and plot a line at the rotation angle alpha until it intersects the circular arc with radius PZII. The resulting osteotomy cut line distance 20 is then marked off on the incisura ischiadica major 21 and ahead on the same arc 22. This gives the polygonal osteotomy line in the os ilium and the minimum distance to the dorsal endpoint E of the osteotomy on the os ischium. The endpoints of the os ischium osteotomy which extends to the foramen obturatum can be freely chosen within a certain range.

FIG. 15 shows an acetabulum fragment rotated according to the construction of FIG. 14. The congruence results from the equiangularity and the equality of the lengths 20 and 22. The small wedge of bone remaining in the foramen ischiadicum according to the cut geometry has been ectomized by extending the cut 20, and the distance to the dorsal endpoint $E_1$ of the os ischium osteotomy has been chosen appropriately greater than 21, in order that in this region as well the osteotomy surfaces will abut each other.

It is understood that when a polygonal osteotomy according to FIGS. 14-16 is used, the transfixion plates are to be configured to match the straight-line course of the osteotomy, particularly as regards the edges of the wedge-shaped transition zone of said plates.

If a point other than the center PZ of the acetabulum is chosen as the center of rotation, a shortening or lengthening of the leg can be achieved as medically indicated.

It may be advantageous in performing the osteotomy, depending on the size and shape of the pelvis, to preoperatively prepare various gauges or patterns (templates) which reproduce the osteotomy polygons for given rotational angles, so that intraoperatively the os ilium can be readily marked (via electrotome) while holding the desired pattern up to it. Similarly, a variety of transfixion plates can be prepared in advance.

Figure 17:
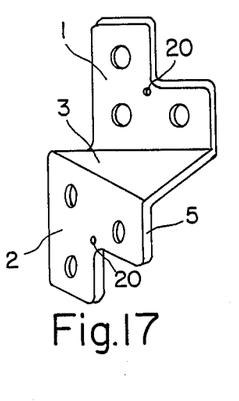
FIGS. 17–19 are perspective views of plates of the invention for use in dogs.
Figure 18:
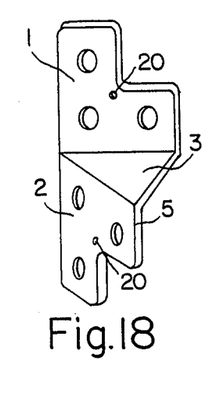
Figure 19:
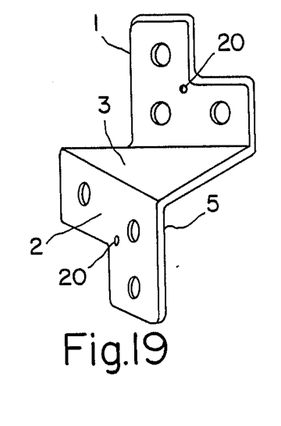

FIGS. 17-19 are carniolateral views of plates for use in dogs subjected to a triple pelvic osteotomy with axial, horizontal rotation of the acetabulum, wherein the course of the osteotomy in the os ilium is perpendicular to the body axis of the dog, i.e. is in the plane of the wedge-shaped zone 3; and the axis around which the acetabulum fragment is swung laterally is parallel to the lumbar region of the spin of the dog. It is seen that here the maximum width of the wedge-shaped zone 3 is on the dorsal edge 5 of the plate. In this way the axis of the swinging may be set up to be close to the center of the acetabulum, thereby achieving the functionally optimum joint geometry for the dog after the rotation of the acetabulum has been completed. The angle of swing, i.e. the angle around the axis between the regions 1 and 2 of the plate, is about 20-70°, preferably 30-60°, and particularly approximately 45°, in a dog. Holes 20 are also provided, for a possible wire loop transfixion element.

We claim:

1. Alone transfixion plate for transfixing an acetabulum fragment to the os ilium, by screw means, following pelvic osteotomies with rotation of the roof of the acetabulum in a human patient comprising:
   a proximal plate region lying substantially in a first plane for application to the os ilium at least generally adapted for close application to a surface of said os ilium;

a distal plate region lying substantially in a second plane for application to the acetabulum fragment at least generally adapted for close application to a surface of said acetabulum fragment; and a substantially wedge-shaped transition zone plate region lying substantially in a third plane intersecting said first and second planes and connecting respective ends of said proximal and distal plate regions for supporting said proximal and distal plate regions at a mutual angle in the range of 10–50 degrees with respect to the ventrodorsal/proximodistal plane the transition zone plate region having larger and smaller width portions and respective sides connected to said proximal and distal plate regions;

the screw-means being disposed in said proximal and distal plate regions.

2. A bone transfixion plate as claimed in claim 1 wherein:
said angle comprises substantially 30°.

3. A bone transfixion plate as claimed in claim 1 wherein:
said plate has a central edge; and
said transition zone plate has region said larger width portion at said ventral edge of the plate.

4. A bone transfixion plate as claimed in claim 3 wherein:
said angle comprises substantially 30°.

5. A bone transfixion plate as claimed in claim 1 wherein:
said wedge-shaped transition zone plate region has a configuration for application against the osteotomy surface of the acetabulum fragment.

6. A bone transfixion plate as claimed in claim 5 wherein:
at least one of said planes is an arcuate plane.

7. A bone transfixion plate as claimed in claim 1 wherein:
said wedge-shaped transition zone plate region has a configuration for application against the osteotomy surface of the os ilium.

8. A bone transfixion plate as claimed in claim 7 wherein:
at least one of said planes is an arcuate plane.

9. A bone transfixion plate as claimed in claim 1 wherein:
said wedge-shaped transition zone plate region has a configuration for application against the osteotomy surfaces of both the acetabulum fragment and the os ilium.

10. A bone transfixion plate as claimed in claim 9 wherein:
said transition zone plate region comprises two wedge-shaped portions respectively extending substantially in said third plane on opposite sides of said proximal and distal plate regions; and
said first and second planes intersect between said two wedge-shaped portions.

11. A bone transfixion plate as claimed in claim 10 wherein:
at least one of said planes is an arcuate plane.

12. A bone transfixion plate as claimed in claim 1 wherein:
said proximal and distal plate regions on respective sides thereof facing the acetabulum fragment join said wedge-shaped transition zone plate region at respective edges; and
each edge has a substantially circular arcuate shape substantially conforming to the osteotomy.

13. A bone transfixion plate as claimed in claim 1 wherein:
said transition zone plate region forms respective obtuse angles with said proximal and distal plate regions.

14. A bone transfixion plate as claimed in claim 1 wherein:
said proximal plate region has a configuration substantially convex on the side thereof applied to the os ilium and
said distal plate region and transition zone each have configurations substantially concave on respective sides thereof applied respectively to the acetabulum.

15. A bone transfixion plate as claimed in claim 1 wherein:
said proximal plate region is longer in the proximal-distal dimension than in the distal region; and
said transition zone plate and distal region plate region are longer than said proximal plate region in the ventral-dorsal dimension.

16. A bone transfixion plate as claimed in claim 1 wherein:
said plate is longer in the proximal-distal dimension than in the ventral-dorsal dimension.

17. A bone transfixion plate as claimed in claim 1 wherein:
said plate is longer in the ventral-dorsal dimension than in the proximal-distal dimension.

18. A bone transfixion plate as claimed in claim 1 wherein:
at least one of said planes is an arcuate plane.

19. A bone transfixion plate as claimed in claim 18 wherein:
each plane is an arcuate plane.

* * * * *